United States Patent [19]

Montano, Jr.

[11] Patent Number: 4,941,877

[45] Date of Patent: Jul. 17, 1990

[54] BALLOON CATHETER

[75] Inventor: Fausto Montano, Jr., Miami Lakes, Fla.

[73] Assignee: Cordis Corporation, Miami Lakes, Fla.

[21] Appl. No.: 302,302

[22] Filed: Jan. 26, 1989

[51] Int. Cl.⁵ ............................................. A61M 29/02
[52] U.S. Cl. ..................................... 604/96; 604/281; 606/194
[58] Field of Search ............................ 604/93, 96-103, 604/266, 271, 281, 282; 128/344, 348.1, 656-658; 606/191-200, 7

[56] References Cited

U.S. PATENT DOCUMENTS

| | | | |
|---|---|---|---|
| 856,093 | 6/1907 | Ong | 604/96 |
| 4,018,231 | 4/1977 | Wallace | 128/351 |
| 4,141,364 | 2/1979 | Schultze | 604/96 |
| 4,292,974 | 10/1981 | Fogarty et al. | 128/344 |
| 4,338,942 | 7/1982 | Fogarty | 128/344 |
| 4,490,421 | 12/1984 | Levy | 428/35 |
| 4,650,466 | 3/1987 | Luther | 604/95 |
| 4,681,092 | 7/1987 | Cho et al. | 128/1 D |
| 4,762,130 | 8/1988 | Fogarty et al. | 128/348.1 |
| 4,820,349 | 4/1989 | Saab | 128/344 |

OTHER PUBLICATIONS

Fowles, Grant R., *Analytical Mechanics*. [Saunders College Publishing, Chicago, 1986], pp. 30, 31.

Primary Examiner—John D. Yasko
Assistant Examiner—Adam J. Cermak
Attorney, Agent, or Firm—Gerstman & Ellis, Ltd.

[57] ABSTRACT

A balloon catheter in which its inflatable and collapsible balloon is of larger diameter than adjacent portions of the catheter body. The balloon defines transition zones at the respective ends which are of fluted shape. Thus, the balloon can assume a collapsed position in which the collapsed transition zones collapse in a substantially star-shaped cross section rather than in a flat-collapsed configuration. Central portions of the catheter follow suit on collapse of the balloon, to avoid the undesired "winging" phenomenon in balloon catheters, particularly PTCA catheters.

22 Claims, 1 Drawing Sheet

BALLOON CATHETER

BACKGROUND OF THE INVENTION

Balloon catheters are used in a variety of medical procedures. For example, in the well-known procedure of percutaneous translumenal coronary angioplasty (PTCA) a balloon catheter is inserted into a coronary artery. Then, the balloon of the catheter is inflated, to force expansion of the walls of the coronary artery to increase the blood flow capacity of the artery, which has been typically reduced by arteriosclerotic lesions.

Catheter balloons for PTCA must be quite strong, to withstand significant inflation pressures. Accordingly, they tend to be somewhat stiff, since their wall thickness must be sufficient to provide the necessary strength. Thus, when deflated, such catheter balloons can flatten in a phenomenon known as "winging", in which the flat, lateral portions of the deflated balloon project laterally outwardly well beyond the rest of the catheter. This is deemed to be undesirable by many practitioners, because of a concern that the flat wings may damage the artery wall as the deflated balloon is advanced through the arterial system into the desired position for inflation. Also, such flat wings can interfere with the manipulation of the catheter and its easy advancement through the arterial system.

In accordance with this invention, an improved balloon configuration for a balloon catheter is provided, to eliminate the undesired "winging" phenomenon which is encountered when the catheter balloon is in deflated condition. Also, the catheter balloon may be stronger than prior art catheter balloons, with improved tensile strength, while exhibiting a reduced wall thickness to improve the flexibility of the balloon. Thus, with the catheter balloon of this invention, PTCA procedures can be performed more effectively, with less concern about damage to coronary arteries by the "winging" phenomenon of the deflated catheter balloon, and with greater ease of catheter advancement through the arterial system.

DESCRIPTION OF THE INVENTION

This invention relates to a catheter having a catheter body, a portion of the body defining an inflatable and collapsible balloon. The balloon is of larger diameter than adjacent portions of the body, and defines transition zones at the respective balloon ends. Typically, the transition zones are areas where the large diameter balloon connects to a smaller diameter catheter tubing, or where the typically cylindrical balloon tapers down to a closed end, if the balloon is at the exact end of the catheter.

In accordance with this invention, at least one of the transition zones is of fluted shape. As a result of this, the balloon can assume a collapsed position in which the fluted, collapsed transition zone or zones define inwardly projecting flutes in a plurality of nonplanar directions, to prevent a flat-collapsed configuration of the balloon.

Typically, from three to eight generally longitudinally directed flutes are present in each transition zone, the flutes being generally uniformly distributed about the circumference of each transition zone. The flutes are generally longitudinally directed at an angle to the balloon axis, and typically extending at a mutually perpendicular radial angle and lateral angle to the axis, the lateral angle being generally from 0 to about 45 degrees, preferably about 10 to 30 degrees. The radial angle in the as-molded balloon is dependent on the length of the transition zone and the relative diameters of the balloon and the connected catheter portions, being typically about 10 to 45 degrees.

When the balloon is in its collapsed position, the inwardly projecting flutes force collapse of the catheter transition zones in directions generally defined by the flutes. Since at least some of the flutes extend inwardly in non-planar relation to other of the flutes, the catheter collapses in a plurality of non-planar directions rather than in the undesired flat collapse, so that widely laterally projecting wings are avoided on collapse.

The central portions of the catheter are directed into a mode of collapse by the flutes that is generally similar to the mode of collapse in the transition zones, so that projecting "wings" are preferably avoided along the entire length of the collapsed catheter balloon. Nevertheless, upon inflation, the catheter balloon readily inflates to its desired, expanded diameter, to perform its conventional function in PTCA, or to be used as desired in any medical procedure involving a balloon catheter, for example as a urinary drainage catheter or the like.

The catheter and its balloon may be made of any conventional, flexible plastic material. However, it is generally preferred for the balloon of the catheter of this invention to be made of polyethylene terephthalate (PET). The catheter balloon of this invention made of PET may be molded in a conventional blow molding process, which may serve to provide biaxial orientation to the balloon for increased strength thereof. Thus, a high strength balloon may be provided, which, because of its high strength, may be of relatively reduced wall thickness when compared with catheter balloons made of other materials. This of course is desirable since it facilitates the passage of the catheter balloon through the arterial system of a patient for desired emplacement at the inflation site, particularly in PTCA procedures.

The balloon may be of generally cylindrical shape, but, if desired, it may alternatively be of oval or other cross-section, of varying diameter and shape along its length.

DESCRIPTION OF SPECIFIC EMBODIMENT

Figure 1:
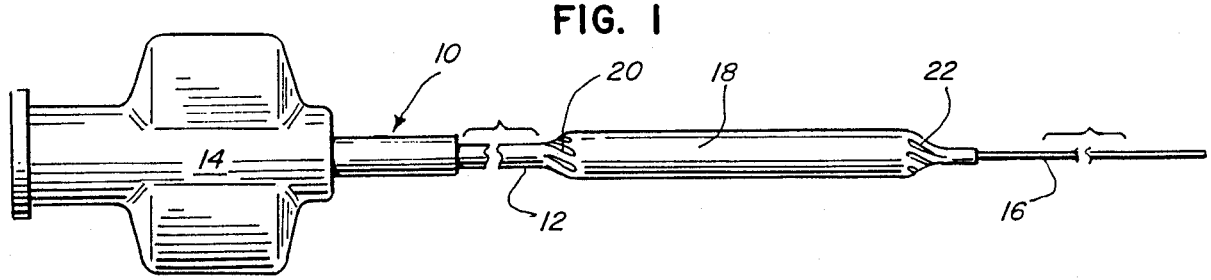
FIG. 1 is a plan view of a PTCA catheter showing the invention of this application.

Referring to the drawings, a balloon catheter is shown, being of a type which is particularly suitable for a PTCA procedure. Catheter 10 may be a conventionally designed PTCA catheter, except as otherwise described herein.

Catheter 10 defines a tubular catheter body 12, a proximal hub 14, and a guide wire 16 which extends through the catheter, all being of generally conventional design. Catheter body 12 defines an inflatable and collapsible balloon portion 18, shown to be, as is conventional, a tubular section of relatively larger diameter than the rest of catheter body 12. Balloon 18 may be an integral part of the rest of the catheter body 12, or it may be separately manufactured, for example by a blow molding process and then attached to the remainder of catheter body 12. Balloon 18 may be internally inflated to expand its diameter, and may also be collapsed to a minimum diameter while, by this invention, the formation of a flat, "winged" configuration may be avoided in the collapsed mode of the balloon.

Figure 2:
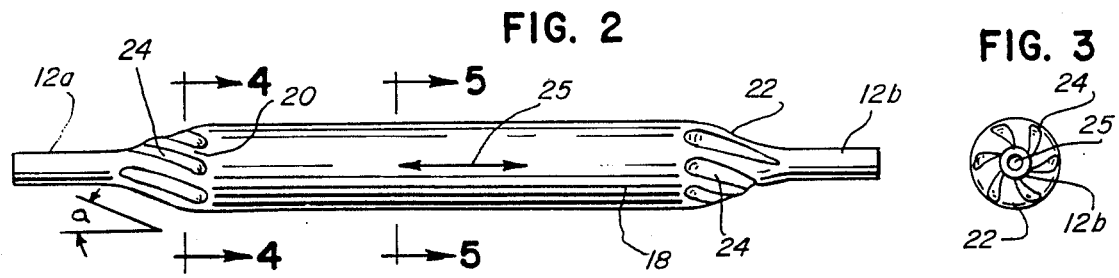
FIG. 2 is an enlarged, plan view of the inflatable and collapsible balloon of the catheter of FIG. 1.
Figure 3:
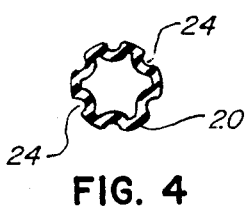
FIG. 3 is an end view of the catheter balloon of FIG. 2.

Balloon 18 defines transition zones 20, 22 at its respective ends, in which the balloon tapers inwardly to the relatively reduced diameters of a proximal portion 12a of the catheter body and a distal portion 12b of the catheter body, as shown in FIG. 2. In accordance with this invention, transition zones 20, 22 each define a plurality of flutes 24, specifically shown as six rounded, generally parallel grooves which are evenly distributed about the circumference of each transition zone 20, 22, and which are disposed in generally longitudinal relation to the axis of balloon 18, specifically being at a lateral angle a (FIG. 7) of about 25 degrees thereto. Flutes 24 also define a radial angle of about 25 degrees, extending radially outwardly relative to the balloon axis 25 in its as-molded configuration, as indicated by FIG. 3. It has been found that the presence of these rounded grooves or flutes 24 serve to prevent the flat, lateral collapse or "winging" of catheter balloon 18 when it is deflated or collapsed.

Figures 4, 5:
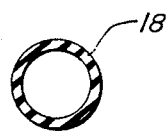
FIG. 4 is a sectional view taken along line 4—4 of FIG. 2
FIG. 5 is a sectional view taken along line 5—5 of FIG. 2.
Figure 8:
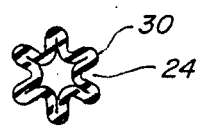
FIG. 8 is a sectional view similar to that of FIG. 4, but showing the catheter balloon in collapsed configuration.

FIG. 4 shows a sectional view of transition zone 20 in its as-molded configuration. Transition zone 22 is of similar shape. Under internal pressure provided through catheter body 12, balloon 18 may expand radially outwardly beyond this configuration. Under exterior compression, or interior suction through catheter body 12, balloon 18 may collapse radially into a collapsed configuration in which transition zone 20 occupies a configuration similar to that shown in FIG. 8, where flutes 24 deepen and are drawn radially inwardly so that the respective transition zones 20, 22 may assume a star shape of reduced diameter. As this takes place, the collapse of the other portions of catheter 18 is directed to prevent the undesired "winging", with formation instead of many lobes 30 projecting radially outwardly in a plurality of non-planar directions.

Thus, it can be seen that the flutes 24, projecting radially inwardly in a plurality of non-planar directions (i.e., a number of directions that cannot be contained in a single plane) serves to prevent the undesired "winging" effect upon collapse of balloon 18.

Catheter balloon 18, and the entire catheter body 12, may be made of PET if desired to provide a higher strength material than has been customarily used in such catheters. Accordingly, the wall thickness of the balloon 18 in its as—molded configuration may preferably be from 0.00035 to 0.0006 inch, which may be less than that of corresponding catheter balloons. Despite that, such a catheter balloon 18 may have equal or improved tensile strength to that of prior art catheter balloons made of polyvinylchloride or the like.

Figure 6:
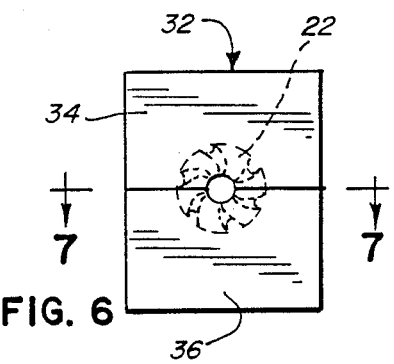
FIG. 6 is an end elevational view of the catheter balloon of this invention, shown in process of manufacture within a blow mold, the blow mold being shown schematically.
Figure 7:
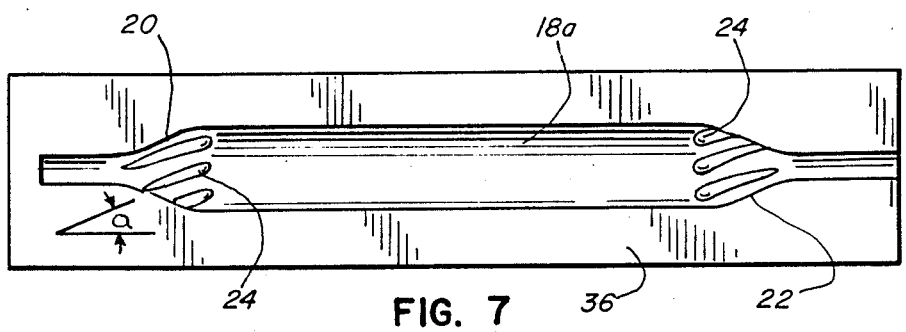
FIG. 7 is a sectional view taken along line 7—7 of FIG. 6.

Catheter balloon 18a is shown in FIGS. 6 and 7 in the process of manufacture by conventional means in a blow mold 32 comprising first and second mold halves 34, 36. Balloon 18a is the same as balloon 18 except that flutes 24 rotate about balloon 18a in the opposite sense from the flutes of balloon 18. A hot parison of PET or the like is placed into the blow mold, and inflated in conventional manner to form catheter balloon 18 or 18a of the desired shape, which shape is governed by the inner shape of the molding chamber of the blow mold 32. In the blow molding process, it is possible to provide biaxial orientation to the PET material, to provide increased strength to the wall of balloon 18 or 18a.

Thus the catheter of this invention may carry a balloon 18 or 18a which is stronger than those of corresponding catheters in current use, and which can collapse in a more compact manner for improvements in the use of the catheter.

If desired, flutes 24 may extend in continuous manner from end to end of balloon 18 or 18a, so that the same, continuous flutes occupy both transition zones 20, 22, if desired.

The above has been offered for illustrative purposes only, and is not intended to limit the scope of the invention of this application, which is as defined in the claims below.

That which is claimed is:

1. In a catheter having a catheter body, a portion of said body defining an inflatable and collapsible balloon, said balloon having a longitudinal axis and being of larger diameter than the adjacent portion of said body and defining transition zones at the respective balloon ends, the improvement comprising, in combination:

at least one of the transition zones being of flute shape, in which said one of the transition zones defines a plurality of radially inwardly projecting flutes about said transition zone, said flutes extending at radial angles to the balloon axis, said flutes also defining lateral angles to the balloon axis to prevent a flat-collapsed configuration of said balloon.

2. The catheter of claim 1 in which each transition zone is connected to a catheter portion of smaller diameter than said balloon.

3. The catheter of claim 1 in which said flutes are generally directed at a lateral angle to the balloon axis of essentially 10 to 45 degrees.

4. The catheter of claim 3 in which said lateral angle is 10 to 30 degrees, said flutes also defining a radial angle to the balloon axis of 10 to 45 degrees.

5. The catheter of claim 1 in which from 3 to 8 flutes are present in each transition zone.

6. The catheter of claim 5 in which said flutes are generally uniformly distributed about the circumference of each transition zone.

7. The catheter of claim 1 which is a PTCA catheter.

8. The catheter of claim 1 in which said balloon is made of polyethylene terephthalate.

9. The catheter of claim 8 in which said polyethylene terephthalate is biaxially oriented.

10. The catheter of claim 1 in which said balloon defines a zone spaced from the ends thereof which is free of said flutes.

11. In a catheter having a catheter body, a portion of said body defining an inflatable and collapsible balloon, said balloon having a longitudinal axis and being of larger diameter than adjacent portions on said body, and defining transition zones at the respective balloon ends, the improvement comprising, in combination;
  said transition zones each defining flutes, said flutes being directed at a substantial radial angle to the balloon axis and at a lateral angle to the balloon axis of essentially 0 to 45 degrees, said ballooning defining a central section that is free of flutes.

12. The catheter of claim 11 in which each transition zone defines from 3 to 8 of said flutes which are generally uniformly distributed about the circumference of each transition zone.

13. The catheter of claim 12 in which each transition zone is connected to a catheter portion of smaller diameter than said balloon.

14. The catheter of claim 13 in which said balloon is made of polyethylene terephthalate.

15. The catheter of claim 14 in which the lateral angle defined by the flutes to the balloon axis is 10 to 30 degrees, said flutes also defining a radial angle to the balloon axis of 10 to 45 degrees.

16. In a catheter having a catheter body, a portion of said body defining an inflatable and collapsible balloon, said balloon having a longitudinal axis and being of larger diameter than adjacent portions of said body and defining transition zones at the respective balloon ends, the improvement comprising, in combination:
  said balloon being made of biaxially oriented polyethylene terephalate, said transition zones defining a plurality of flutes generally directed at a lateral angle to the balloon axis of essentially 10 to 45 degrees.

17. The catheter of claim 16 in which from 3 to 8 flutes are present in each transition zone.

18. The catheter of claim 17 in which said flutes are generally uniformly distributed about the circumference of each transition zone.

19. The catheter of claim 18 in which each transition zone is connected to a catheter portion of smaller diameter than said balloon.

20. The catheter of claim 19 in which the lateral angle of said flutes to the balloon axis is 10 to 30 degrees.

21. The catheter of claim 20 in which said balloon defines a zone spaced from the ends thereof which is free of said flutes.

22. The catheter of claim 16 which is a PTCA catheter.

* * * * *